US005810004A

United States Patent [19]

Ohki et al.

[11] Patent Number: 5,810,004

[45] Date of Patent: Sep. 22, 1998

[54] MEDICATOR FOR A CAPSULE FILLED WITH A POWDERED DRUG

[75] Inventors: Hisatomo Ohki; Shigemi Nakamura, both of Isesaki; Kazunori Ishizeki, Fujimi; Akira Yanagawa, Yokohama, all of Japan

[73] Assignees: Unisia Jecs Corporation, Atsugi; Dott Limited Company, Yokohama, both of Japan

[21] Appl. No.: 731,111

[22] Filed: Oct. 9, 1996

[30] Foreign Application Priority Data

Oct. 9, 1995 [JP] Japan .................................... 7-287923

[51] Int. Cl.$^6$ ......................... A61M 15/00; A61M 16/00; B05D 7/14; B65D 83/06

[52] U.S. Cl. ............................... 128/203.15; 128/203.21; 128/203.28

[58] Field of Search ......................... 128/203.12, 203.15, 128/203.19, 203.21–203.24

[56] References Cited

U.S. PATENT DOCUMENTS

| | | | |
|---|---|---|---|
| 2,147,158 | 2/1939 | Goldenthal | 128/266 |
| 2,992,645 | 7/1961 | Fowler | 128/208 |
| 3,906,950 | 9/1975 | Cocozza | 128/203.21 |
| 3,949,751 | 4/1976 | Birch et al. | 128/203.21 |
| 5,366,122 | 11/1994 | Guentert et al. | 222/401 |

FOREIGN PATENT DOCUMENTS

| | | |
|---|---|---|
| 0 303 844 | 2/1989 | European Pat. Off. . |
| 0 530 625 | 3/1993 | European Pat. Off. . |
| 3-66382 | 3/1991 | Japan . |
| 1 436 028 | 5/1976 | United Kingdom . |

*Primary Examiner*—Kimberly L. Asher
*Attorney, Agent, or Firm*—Foley & Lardner

[57] ABSTRACT

A medicator for a capsule filled with a powdered drug, comprising: a first member adapted to receive a capsule therein; a second member, having an air supply valve structure, arranged to communicate with the first member and arranged to operatively discharge air sucked from outside the medicator towards the first member in which a capsule is received; an air stream passage formed within the first member and the second member to direct air discharged from the air supply valve structure in a direction towards a capsule received by the first member; a third member removably attached to the first member to spray powdered drug in a capsule out of the medicator with air discharged from the air supply valve structure via the air stream passage; a drug trapping structure formed in the air stream passage to trap part of powdered drug contained in a capsule which falls down into the drug trapping structure; and a drug collecting structure formed in the air stream passage between the drug trapping structure and the air supply valve structure to collectively dam powdered drug from a capsule which falls in a direction opposite to the first member together with air when the air supply valve structure is in an intermediate state between a fully open state and a fully closed state, thereby preventing powdered drug from entering the air supply valve structure.

12 Claims, 6 Drawing Sheets

MEDICATOR FOR A CAPSULE FILLED WITH A POWDERED DRUG

BACKGROUND OF THE INVENTION

The present invention relates to a medicator suitable for dosing a powdered drug filled within a capsule into an internal body of a patient.

Generally, a method for dosing a powdered drug for a patient having a bronchial allergy or asthma via his or her nose or mouth so as to make a medical treatment for such a sickness as described above has been adopted. In addition, in this curing method, a self-contained spray is used to dose the powdered drug filled within the capsule into the patient's nose and mouth (nostrils and oral cavity).

A Japanese Patent Application First Publication No. Heisei 3-66382 exemplifies the above-described self-contained spray used for dosing the powdered drug, for example, into the internal of the patient's internal body via his or her nose (nostrils).

In the spray disclosed in the above-identified Japanese Patent Application, a pump chamber is installed within an entrance side of a ventilation chamber and a powdered body housing chamber for housing the capsule is installed at an exit side of the ventilation chamber. Then, a spray hole is formed at a front end of the powdered body housing chamber. In addition, an encapsulation is detachably fitted to the powdered housing chamber. A long steeple extended axially along the encapsulation within the encapsulation serves to penetrate into the capsule housed into the powdered housing when the encapsulation is mounted into the front end of the powdered housing chamber to provide therein. Furthermore, a movable valve is installed for passing the pressure stream from the pump chamber toward the powdered body housing chamber and blocking the stream of the pressure air in the direction opposite to the flow of the pressure air is mounted on a ventilation passage within the ventilation chamber.

When a holing is carried out in the capsule, the capsule in which the powdered drug is filled is housed in the powdered body housing and thereafter the steeple is penetrated into a spray hole of the powdered housing to mount the encapsulation from the front end of the powdered body housing chamber. The steeple makes a ventilation hole penetrating in an axial direction of the capsule.

Next, to dose the powdered drug, the encapsulation is removed from the powdered body housing chamber, the front end of the powdered housing chamber is inserted into the nose hole of the patient, the pump chamber is pressurized so that the air from the pump chamber is communicated within the capsule via the communication passage in the ventilation chamber, the air causing the drug in the capsule being sprayed into one of the nose holes of the patient through a spray hole. The patient inserts alternatingly the front end portion of the powdered body housing chamber to repeat the pressure operation on the pump chamber so that the dosing of the drug into the left and right nose holes is carried out. On the other hand, during the dosing operation and when the pump chamber is reformed into the original configuration (the pump chamber sucks the external air), the air is streamed from the spray hole of the powdered body housing chamber and is streamed in the opposite direction together with the drug. However, the movable valve prevents the drug from invading into the pump chamber.

However, since it requires a slight time for the movable valve to move from a fully open state to a fully closed state, the drug is streamed in the opposite direction during the time when the movable valve is moved to the fully closed position to be sticked to the movable valve. A repetitive use of the spray causes the drug to be accumulated onto the movable valve so that the movable valve fails to open and the drug is streamed into the pump chamber. Consequently, since the part of the drug filled within the capsule is streamed into the pump chamber, a required amount of the drug for the patient cannot be dosed and an effect of the drug on the patient's internal body is reduced.

SUMMARY OF THE INVENTION

It is an object of the present invention to provide an improved mediator for a capsule in which a powdered drug is filled which can assure a prevention of part of the powdered drug from being introduced into a pump chamber having an air supply valve structure and can dose a required amount of drug into a patient's internal body.

In order to accomplish the aforementioned object, there is provided with a medicator for a capsule in which a powdered drug is filled comprising: a first member arranged so as to be capable of receiving said capsule therein; a second member, having an air supply valve structure, arranged so as to enable to be communicated with the first member and arranged so as to enable to operatively discharge an air sucked from external of the medicator toward the first member in which the capsule is received; an air stream passage formed within said first member and said second member so as to enable to direct the air discharged from said air supply valve structure in a direction toward the capsule received by said first member; a third member removably attached onto the first member so as to enable to spray of the powdered drug in said capsule toward an external direction of the medicator with the air discharged from the air supply valve structure via the air stream passage; a drug trapping structure formed in said air stream passage so as to enable to trap part of the powdered drug in said capsule which falls down thereinto from the capsule; and a drug collecting structure formed in said air stream passage between the drug trapping structure and the air supply valve structure so as to collectively dam the powdered drug in said capsule which is streamed in a direction opposite to the first member together with the air streamed when the air supply valve structure is in an intermediate state between a fully open state and a fully closed state, thereby preventing the powdered drug from being invaded into the air supply valve structure.

BEST MODE FOR CARRYING OUT THE INVENTION

Reference will hereinafter be made to the drawings in order to facilitate a better understanding of the present invention.

FIGS. 1 through 5 show a first preferred embodiment of a medicator for a capsule in which a powdered drug is filled according to the present invention.

In FIGS. 1 through 5, a capsule holder 1 is provided for receiving the capsule in which the powdered drug is filled.

The capsule holder 1 includes a fixed member 2 formed in a double cylindrical shape and a movable member 9 movably disposed in an axial direction of the fixing member 2.

Figure 1:
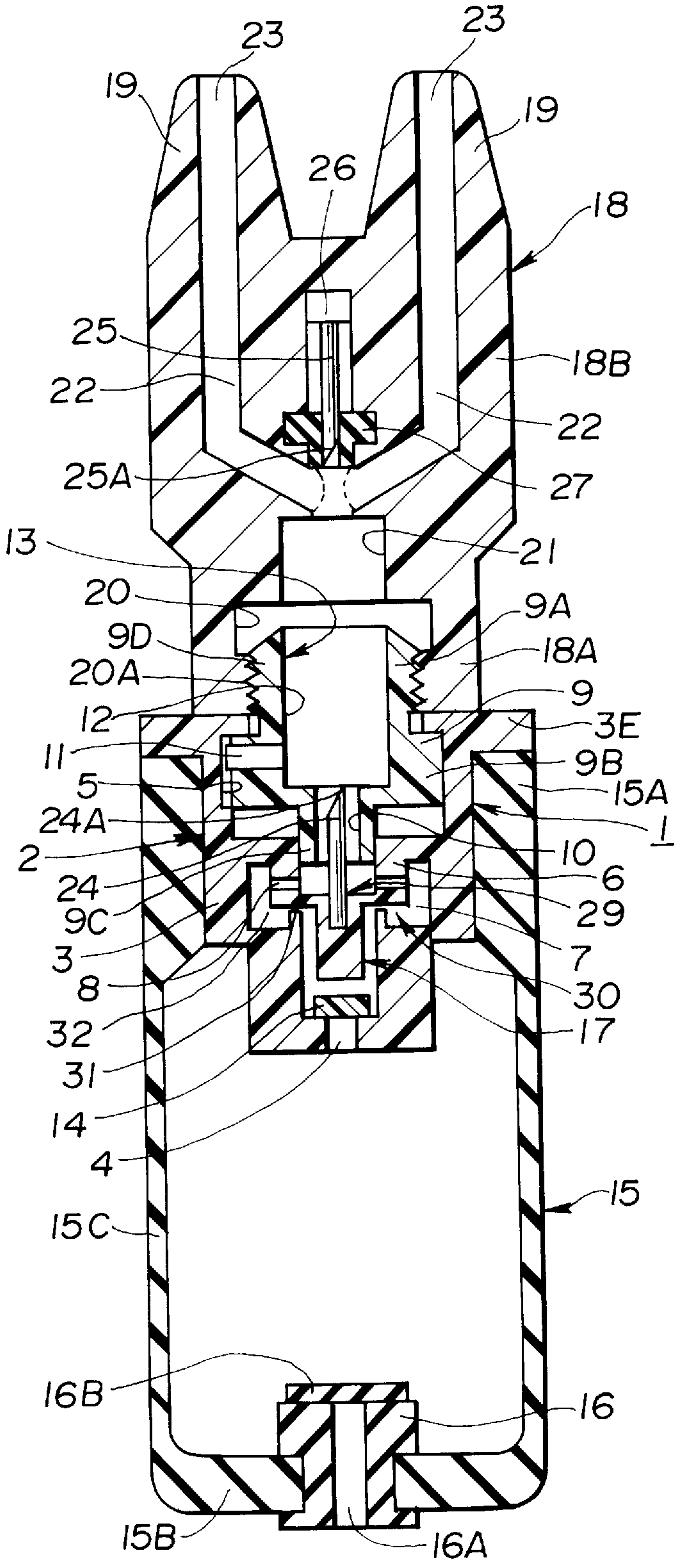
FIG. 1 is a whole cross sectional view of a mediator for a capsule in which a powdered drug is filled in a first preferred embodiment according to the present invention.
Figure 3:
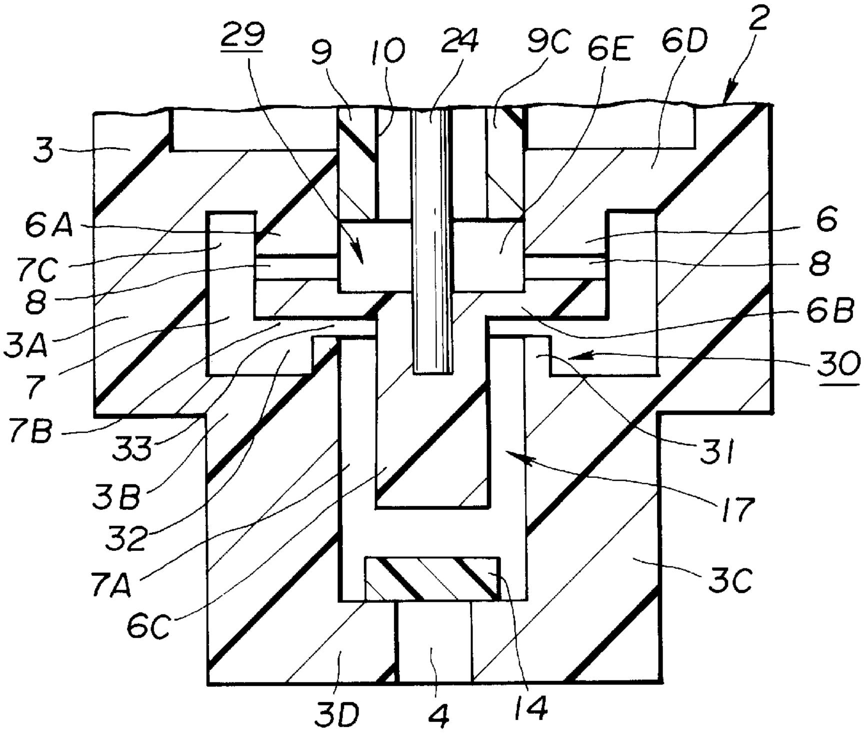
FIG. 3 is an expanded cross sectional view of a capsule holder part of the medicator shown in FIG. 1.

The fixing member 2 includes, as shown in FIG. 3, an outer envelope 3 formed cylindrically with an opening directed toward an upper direction as viewed from FIG. 1. The outer envelope 3 includes: a large-diameter envelope portion 3A; a bottom portion 3B of the large-diameter envelope portion 3A; a small-diameter envelope portion 3C continued from the bottom portion 3B and extended downward from the bottom envelope portion 3B; a lowest bottom portion 3D provided at the end of the small-diameter envelope portion 3C; and a flange portion 3E formed at an end of the opening of the large-diameter envelope portion 3A, the flange portion 3E substantially serving to stop a dropping of a movable member 9 which is moved in an axial direction of the large-diameter envelope portion 3A along an internal periphery of the envelope portion 3A and serving to position a pump portion 15 as will be described later which is disposed so as to enclose the fixing member 2 from its outer peripheral side thereof. In addition, the lowest bottom portion 3D is formed with an air supply passage 4 which is opened within the pump portion 15. An engagement groove 5 which engages a pin 11 is extended in the axial direction of the movable member 9. The pin 11 serves to block the rotation of the movable member 9 with respect to the fixing member 2. An inner envelope portion 6 is disposed within the outer envelope portion 3. The inner envelope portion 3 includes an envelope portion 6A, a lower projected portion 6C extended in a downward direction from a bottom portion 6B of the envelope portion 6A so as to limit the degree of opening of an air supply valve 14 as will be described later, a crocodile portion 6D whose diameter is extended from the opening side of the envelope portion 6A, and a hole portion 6E enclosed by a wall of the envelope portion 6A and by a wall of the bottom portion 6B. The inner envelope portion 6 is linked to an inner periphery of the large-diameter envelope portion 3A of the outer envelope 3 via the crocodile portion 6D. In addition, the lower projected portion 6C is contacted with the air supply valve body 14 so as to limit the degree of opening of the air supply valve 14 (lift variable of the air supply valve 14).

A bend passage 7 is formed between the outer envelope portion 5 and the inner envelope portion 6 and is a part of an air stream passage. The bend passage 7 includes a first passage 7A having a smaller diameter, extended along the axial direction of the inner envelope portion 6, and formed on an outer peripheral surface of the lower projected portion 6C, a second passage 7B bent in the upward direction from the upper end of the first passage 7A whose diameter is extended toward the outside in the radial direction of the second passage, and a third passage 7C extended in the upward direction from the outer peripheral end of the second passage 7B. The first passage 7A has its lower end communicated with the air supply passage 4 via the air supply valve 14.

Respective ventilation passages 8 are provided on the inner envelope portion 6, the respective ventilation passages 8 being diametrically fitted to the envelope portion 6 so as to communicate the third passage 7C with a drug trap portion 29 as will be described later.

The movable member 9 is movably disposed in the axial direction of the fixing member 2, the movable member 9 including the envelope portion 9A; a large-diameter bottom portion 9B provided at a lower end of the envelope portion 9A so as to be held movably along the axial direction within the large-diameter envelope portion 3A of the outer envelope 3, and a projection portion 9C extended within the envelope 6A of the inner envelope portion 6 from a center of the bottom portion 9B. A male screw 9D is inscribed over a whole periphery of an inner peripheral surface of the envelope portion 9A. A first steeple inserting hole 10 through which a first steeple 24 is penetrated is provided along an axial direction of the small-diameter projection portion 9C and is penetrated through the bottom portion 9B into the envelope portion 9A. The pin 11 is projected in an outward direction of the envelope portion 9A from an outer peripheral end of the envelope portion 9. The pin 11 is engaged with the engagement groove 5 of the fixing member 2 so that the movable member 9 is allowed to be axially shifted with respect to the fixing member 2 and the rotation of the movable member 9 with respect to the fixing member 2 is limited.

Figure 4:
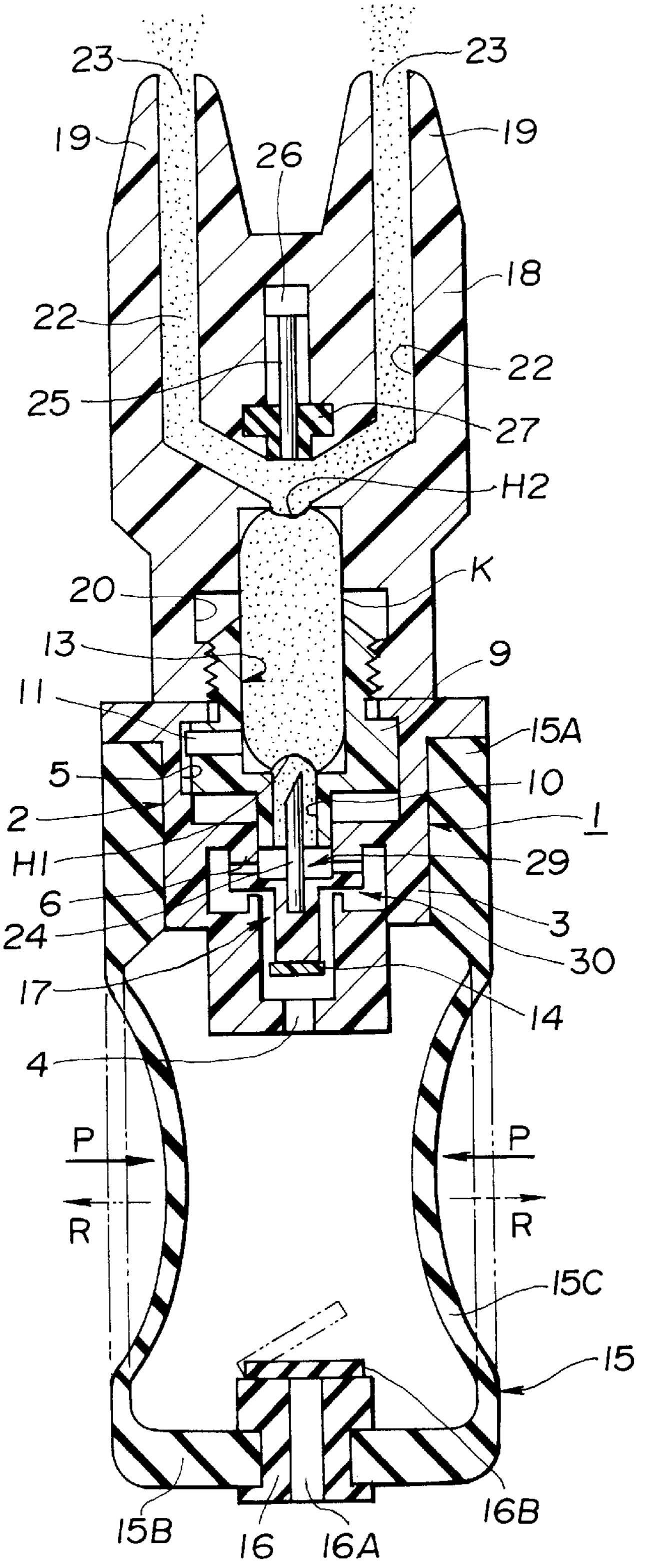
FIG. 4 is a cross sectional view of an essential part as FIG. 1 for indicating a state in which the drug within the capsule is sprayed by pressing a pump portion.

On the other hand, a one-sided capsule hole 12 having a slightly larger diameter than the capsule K (as shown in FIG. 4) is formed within an inner peripheral side of the envelope portion 9A of the movable member 9. The one-sided capsule hole 12 is integrated with the other-sided capsule hole 21 to constitute a capsule receiving hole 13.

In the capsule holder 1 in the first embodiment, the movable member 9 is movable in the axial direction along the outer envelope portion 3 of the fixing member 2. In addition, when the male screw 9D of the movable member 9 is screwed into the female screw 20A, the rotation of the movable member 9 with respect to the fixing member 2 is limited by means of the rotation stop pin 11 so that the movable member 9 is automatically drawn up toward a spray passage forming member 18.

The air supply valve 14 having a valve body 14 is installed within the small-diameter envelope portion 3C so as to open or close the air stream passage 4 formed on the fixing member 2. When the air is supplied from the pump portion 15, the air supply valve 14 is open (the valve body reaches to the lower projected portion 7A). When the air is sucked into the pump portion 15, the valve body is seated so as to close the air supply passage 4.

The pump portion 15 is formed cylindrically of a rubber material. The pump portion 15 includes: a thick opening portion 15A, a bottom portion 15B, and a pressable (flexible) portion 15C formed between the thick opening portion 15A and the bottom portion 15B. The thick opening portion 15A is air-tightly attached onto the large-diameter envelope portion 3A of the outer envelope portion 3. In addition, almost all parts of the capsule holder 1 is housed in the pump portion 15 so that the medicator can be miniaturized in the axial direction.

A suction valve structure 16 is provided on the bottom portion 15B of the pump portion 15. The suction valve structure 16 includes: a suction passage 16A located at a center portion of the bottom portion 15B so as to be communicated within the pump portion 15; and a valve body 16B which is closed when the pressable portion 15C is pressed under pressure by an operator (patient) to supply the air external of the medicator in the pump portion 15 to the grasped capsule and is opened when the pressable portion 15C is returned from the pressed state to the originally shaped position to suck the external air into the pump portion 15.

An air stream passage 17 is formed having the air supply passage 4, the bend passage 7, each passage 8, and the hole 10 into which the steeple is extended.

The air stream passage 17 serves to flow the air supplied from the pump portion 15 toward the capsule K held in the capsule holder 1.

The spray formed passage member 18 is disposed on the movable member 9 of the capsule holder 1. The capsule holder 1 includes a small-diameter portion 18A located at a lower end of the capsule holder 1 and a large-diameter portion 18B located at an upper end of the capsule holder 1. A pair of left and right spray nozzles 19 and 19 are formed and projected on an upper end of the large-diameter portion 18B.

A screw hole 20 is formed for the movable member 9 on the small-diameter portion 18A and the female screw 20A which is to be screwed into the male screw 9D of the movable member 9 is formed in the inner periphery of the opening side of the screw hole 20. The other-sided capsule hole 21 is formed on a depth portion of the screw hole 20 and constitutes the capsule receiving hole 13 together with the one-sided capsule hole 12.

A pair of left and right drug passages 22 and 22 are formed on the spray formed passage member 18. Each drug passage 22 is formed in a substantially U shaped passage having a common passage at a basic end portion thereof and having branched passages at a tip end thereof. The branched passages provide spray exits 23 and 23 at the tip end thereof, separately.

The first steeple 24 serves to hole a lower end of the capsule K with a pin and is extended in the fixing member 2, the first steeple 24 having a base end secured onto the lower projected portion 6C of the inner envelope portion 6 at its basic end thereof and a tip end projected from the bottom end of the hole 13 toward the opening of the hole and formed in a sharp needle 24A.

The first steeple 24 has the sharp needle at its tip projected from the bottom portion of the capsule receiving hole 13 when the movable member 9 is positioned at the pump portion 15. In this state, when the capsule K is inserted under pressure into the capsule receiving hole 13 so that an air streaming hole H1 (as shown in FIG. 4) is formed on the capsule K.

On the other hand, when the movable member 9 is placed at the spray formed passage member 18 side, the tip 24A of the first steeple 24 is retracted into the pin inserting hole 10 so that the tip 24A of the first steeple 24 is drawn out from the air streaming hole H1. At this time, the first steeple 24 is positioned at the pin inserting hole 10 and a flow passage area formed on the pin inserting hole 10 is throttled. Therefore, the pin inserting hole 10 permits the air stream velocity of the air from the pump portion 15 to be increased so that the air stream velocity increased permits the drug in the capsule K to be stirred effectively.

Figure 2:
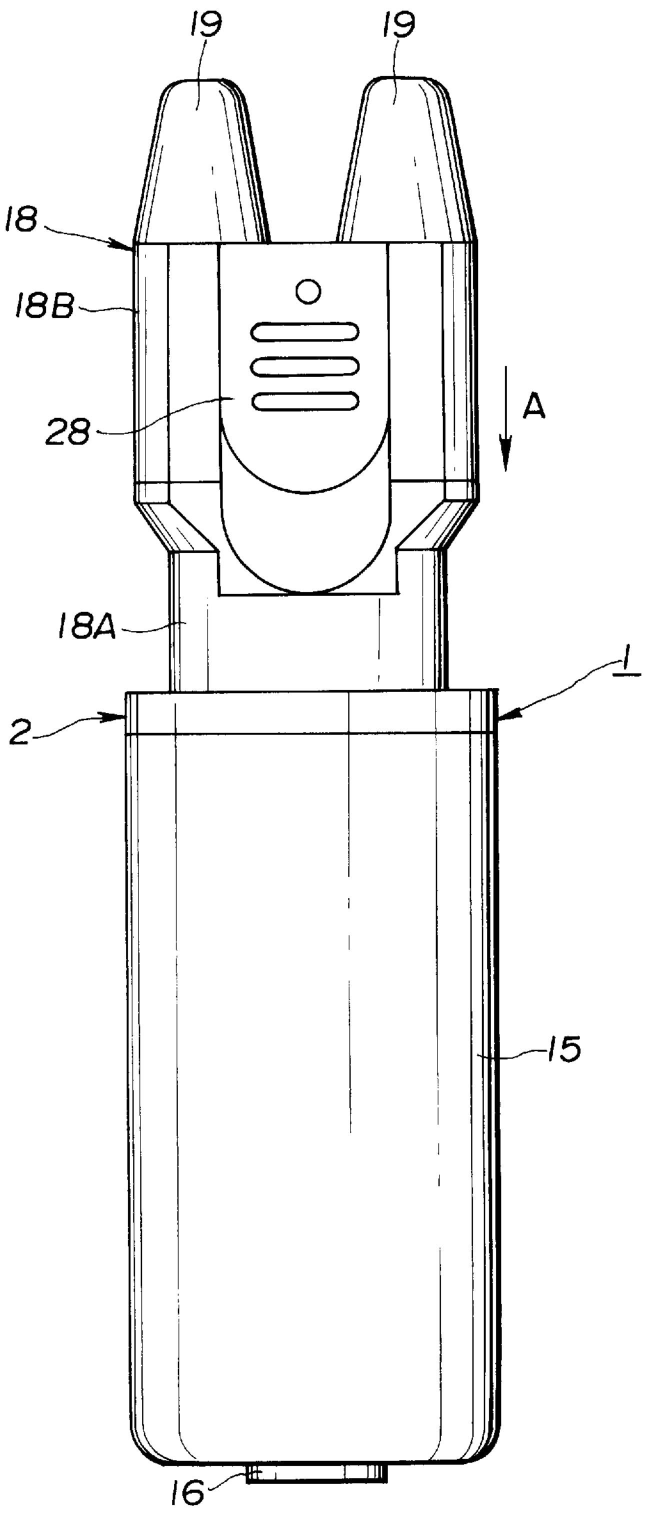
FIG. 2 is an outer appearance view of a third member (a spray passage formed member) the mediator shown in FIG. 1.

A second steeple 25 is provided in the spray formed passage member 18 so as to face toward the first steeple 24. A basic end of the second steeple 25 is secured on a slide block 26 which is slidably and axially disposed. The tip of the second steeple 25 is extended so as to be enabled to penetrate into a seal rubber 27 and is formed in a sharp needle 25A. The slide block 26 is connected to an operation plate 28 (as shown in FIG. 2) which is disposed outside of the spray formed passage member 18 in order to operate the second steeple 25. The second steeple 25 is moved in an arrow-marked direction A in FIG. 2 via the slide block 26 when the operation plate 28 is moved in the arrow-marked direction of A shown in FIG. 2. The tip 25A of the second steeple 25 is used to penetrate the capsule K to form an air streaming out hole H2.

A dropped drug trapping portion 29 is provided on the bottom portion 29 of the hole portion 6E of the inner envelope portion 6, the dropped drug trapping portion 29 serving to trap the dropped drug from the air streaming hole H1 penetrated in the capsule K by means of the first steeple 24 with the position of the medicator approximately vertical with respect to the ground as viewed from FIGS. 1 to 5. Consequently, the dropped drug trapping portion 29 can prevent the powdered drug dropped from the capsule K from being invaded into the air supply valve structure 14. In addition, the powdered drug trapped within the dropped drug trapping portion 29 is supplied to the patient together with part of the powdered drug in the capsule K according to the air supplied from each ventilation passage 8 during the drug spray.

A reverse flow damming portion 30 is formed between the outer envelope portion 3 and the inner envelope portion 6. The reverse flow damming portion 30, in the first embodiment, includes an annular projected wall portion 31 located on an inner diameter side of the radially extended passage 7B of the bend passage 7 and projected upward from the bottom portion 3B of the outer envelope 3 and a drug collecting space 32 formed by damming the radially extended passage 7B with the projected wall portion 31. It is noted that a throttling passage 33 is formed between the projected wall portion 31 and the bottom portion 6B of the inner envelope portion 6.

The reverse flow drug collecting portion 30 circulates the air including the powdered drug with the radially extended passage 7B and dams the air including the powdered drug with the projected wall portion 31 when the powdered drug is flowing in the direction opposite to the spray formed passage member 18 together with the air so as to collect the powdered drug in the air into the drug collecting space 32, thus preventing the powdered drug from being adhered (sticked) onto the air supply valve structure 14 and from being invaded into the pump portion 15. In addition, the throttling passage 33 acts a circulation resistance on the circulating air toward the pump portion 15 so that the reverse flow of the air toward the pump portion 15 itself can be suppressed and the reverse flow of the powdered drug can be prevented.

On the other hand, the drug collected within the drug collecting space 32 is supplied to the patient together with the powdered drug in the capsule K and within the dropped drug trapping portion 29 by means of the air discharged from the pump portion 15 during the drug spray.

An operation of the medicator described in the first embodiment when the medicator is used to dose the powdered drug into the internal body of the patient will be described below.

First, the movable member 9 of the capsule holder 1 is positioned at the pump portion 15 and the tip 24A of the first steeple 24 is projected toward the bottom end of the capsule receiving hole 13. In this sate, the capsule K is inserted into the capsule receiving hole 13 and with the patient's finger the capsule K is pressed into the capsule receiving hole 13. Thus, the tip 24A of the first steeple 24 is pecked (penetrated) into the capsule K so that the capsule K is formed with the air streaming hole H1.

Next, to assemble the spray formed passage member 18 into the capsule holder 1, the female screw 20A is screwed into the male screw 9D at the capsule holder 1. Thus, the movable member 9 of the capsule holder 1 is moved toward the spray formed passage member 18 by means of the screw in the spray formed passage member 18 so that the capsule K is pressed and held within the capsule receiving hole 13 slightly pressured in the axial direction of the holder 1. At this time, the tip 24A of the first steeple 24 which has been penetrated into the capsule K to form the air streaming hole H1 is drawn from the capsule K so that the capsule K is communicated with the bend passage 7 via the air streaming hole H1, the hole 10, and each ventilation passage 8.

When the first steeple 24 is drawn from the capsule K, the drug within the capsule K is dropped from the air streaming hole H1 into the inner envelope 6. However, the dropped drug is trapped within the dropped drug trapping portion 29 formed within the inner envelope portion 6.

Furthermore, in order to form the air streaming hole H2 is formed within the capsule K, the operation plate 28 is moved in the arrow-marked direction A shown in FIG. 2 so that the second steeple 25 is moved toward the capsule K and the tip 25A of the second steeple 25 is pressed to penetrate the capsule K to form the air streaming hole H2. Thereafter, with the operation plate 28 returned to the original position, the tip 25A of the second steeple 25 is drawn from the capsule K. Consequently, the holing operations for the capsule K have been carried out to prepare for the dosing of the powdered drug into the internal body of the patient.

Next, the dosing operation for the powdered drug within the capsule K to be dosed into the nostrils of the patient after the holing operations for the received capsule K will be described below.

First, each spray nozzle 19 is inserted into the corresponding one of the patient's nostrils and, as shown in FIG. 4, the pressable (flexible) portion 15C is pressed (squeezed) in the arrow-marked direction P so that the air stream is generated from the pump portion 15, this air being acted upon the air supply passage 4 so that the air supply valve structure 14 is pressed onto the lower projected portion 6C to open the air supply valve structure 14. Thus, the pressed air is streamed into the capsule K from the air streaming hole H1 via the air supply passage 4, the bend passage 7, each air stream passage 8, and hole 10. The air streamed into the capsule K stirs the drug to form a drug mixed air. The drug mixed air is sprayed the pair of the left and right nozzles 23 and 23 via the air streaming hole H2 and the pair of the left and right drug passages 22 and 22 so that the powdered drug can be dosed simultaneously into the left and right nostrils of the patient.

On the other hand, if the force applied onto the pressable portion 15C of the pump portion 15 is released, the pressable portion 15C is returned to the original shape in the arrow-marked direction R by means of an elastic force thereof, as shown in a dot-and-dash line of FIG. 4 so that the pump portion 15 indicates a negative pressure to open the valve body 16B of the suction valve structure 16, the external air being sucked into the pump portion 15 via the suction passage 16A.

It is noted that although the valve body of the supply valve structure 14 is seated onto the air supply passage 4 due to the generated negative pressure within the air pump portion 15 to close the air supply passage 4, the external air is slightly sucked from each spray nozzle outlet 23 during the time when the air supply valve structure 14 is transferred from the fully open state to the fully closed state so that the external air is streamed in the direction opposite to the nozzle outlets 23 toward the bend passage 7 via each ventilation passage 8 together with the drug trapped within the dropped drag trapping portion 29.

Figure 5:
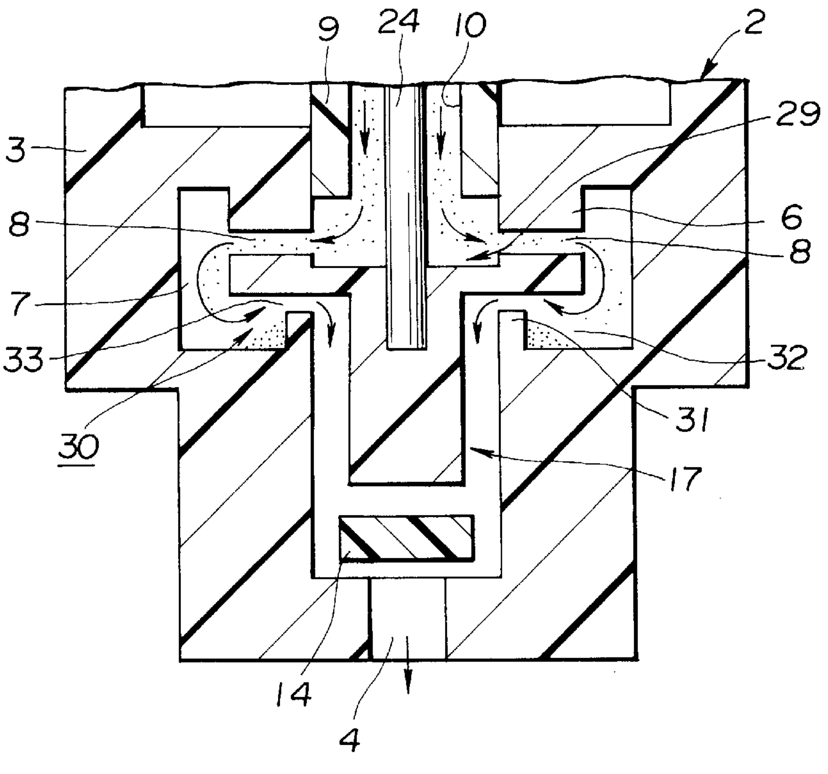
FIG. 5 is a cross sectional view viewed at the same position as FIG. 3 for indicating a flow of the sprayed powder of drug when a pump portion is returned to an original position.

However, in the first embodiment, the projected wall portion 31 is disposed on the radially extended passage 7B of the bend passage 7. Thus, as shown in FIG. 5, the part of the powdered drug which is reverse streamed can be dammed with the projected wall portion 31 to collect the reverse streamed drug into the drug collecting space 32. In addition, since the throttling passage 33 is formed in the passage between the projected wall portion 31 and the bottom portion 6B of the inner envelope portion 6, the throttling passage 33 acts the circulation resistance on the air circulating toward the pump portion 15. Hence, the reverse flow of the air toward the pump portion 15 itself can be suppressed and the reverse stream of the powdered drug into the pump portion 15 via the air supply valve structure 14 can be prevented.

On the other hand, the powdered drug trapped into the dropped drug trapping portion 29 and dammed within the drug collecting space 32 can be supplied to the patient's internal body according to the air discharged from the pump portion 15 during the spray of the powdered drug together with the drug present within the capsule K.

Since, in the first preferred embodiment of the medicator for the capsule K in which the powdered drug is filled, the dropped drug trapping portion 29 is formed within the inner envelope portion 6 and the reverse streamed drug collecting portion 30 is interposed in the midway through the air stream passage 17, the reverse streamed drug collecting portion 30 being constituted by the projected portion 31 defining the drug collecting space 32, the drug dropped from the capsule K can be trapped onto the dropped drug trapping portion 29 and the drug streamed in the direction toward the pump portion 15 together with the air reverse streamed during the return of the pressable portion 15C of the pump portion 15 into the original shape can be dammed by means of the projected wall portion 31 of the reverse streamed drug collecting portion 30 so as to collect the reverse streamed drug into the drug collecting space 32. Consequently, the powdered drug can be prevented from being circulated into the pump portion 15 at two stages.

Consequently, a valve open failure of the air supply valve structure 14 due to the sticks and accumulation of the powdered drug onto the valve body of the air supply valve structure 14 streamed from the capsule K can be prevented and the invasion of the powdered drug into the pump portion 15 can be blocked.

In addition, since the throttling passage 33 is formed to act the air circulation resistance on the air circulated toward the pump portion 15 at the reverse streamed drug collecting portion 30, the reverse flow of the air toward the pump portion 15 itself can be suppressed. In this respect, the invasion of the drug into the pump portion 15 can be prevented as well.

Furthermore, since the part of the powdered drug trapped into the dropped drug trapping portion 29 and the part of the powdered drug collected within the drug collecting space 32 can be supplied to the patient contacted with the nozzle outlets 23 and 23 together with the drug left within the capsule K according to the air discharged from the pump portion 15 during the spray of the powdered drug, the required amount of the drug can be dosed for the patient and the efficiency of the drug can be increased.

It is noted that since the drug collecting space 32 is defined by the projected wall portion 31, the part of the powdered drug collected within the drug collecting space 32 can temporarily be collected. Even if the medicator is inclined with respect to the vertical direction of the ground, the collected drug can be prevented from being dropped into the pump portion 15. Consequently, a handling of the medicator becomes facilitated.

On the other hand, tools to hole the capsule K are incorporated into the medicator itself and the drug operation can be carried out without removal of the tools. Thus, the attaching and detaching operations of the tools required in the case of the medicator disclosed in the Japanese Patent Application First Publication No. Heisei 3-66382 can be omitted. In addition, the tools cannot be lost and handling safety can be improved.

Figure 6:
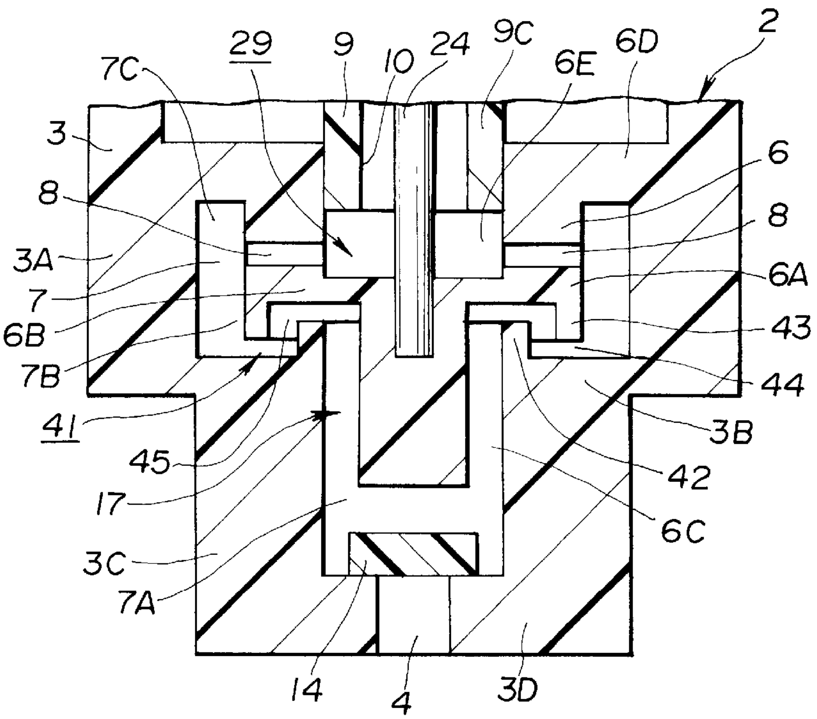
FIG. 6 is a cross sectional view of an essential part of an air stream passage in a second preferred embodiment of the medicator according to the present invention.

FIG. 6 shows a second preferred embodiment of the medicator for the capsule in which the powdered drug is filled according to the present invention.

Only the difference from the first embodiment shown in FIGS. 1 to 5 will be described herein.

In the second embodiment shown in FIG. 6, the projected wall portion includes two projected wall portions as will be described below.

That is to say, the reverse streamed drug collecting portion 41 in the second embodiment includes: a) an annular small-diameter projected wall portion 42 projected in the upward direction as viewed from FIG. 6 from the bottom portion 3B of the outer envelope 3 and located at the small diameter side of the radially extended passage 7B; b) an annular large-diameter projected wall portion 43 projected in the downward direction from the bottom portion 6B of the inner envelope portion 6 and located at the outer diameter side of the radially extended passage 7B; and c) the drug collecting space 44 formed by damming the radially extended passage 7B with the projected wall portions of 42 and 43. Thus, the throttling passage 45 of a crank shape in cross section is formed between the small-diameter projected wall portion 42 and the bottom portion 6B of the inner envelope portion 6, between the large-diameter projected wall portion 43 and the bottom portion 3B of the outer envelope portion 3, and between the small-diameter projected wall portion 42 and the large-diameter projected wall portion 43.

The advantages of the second embodiment are generally the same as those in the first embodiment. Especially, in the second embodiment, since the small-diameter projected wall portion 42 and the large-diameter projected wall portion 43 are overlapped, the prevention of the part of the powdered drug which is streamed toward the direction opposite to the nozzle outlets 23 and 23 from being streamed into the air supply valve structure 24 can more positively be assured by the double structure of the projected wall portions 42 and 43. In addition, since the throttling passage 44 is formed of the crank shape in cross section, the circulation resistance due to the throttling passage 44 can be increased, the more suppression of the reverse flow of the air toward the pump portion 15 can be assured.

Figure 7:
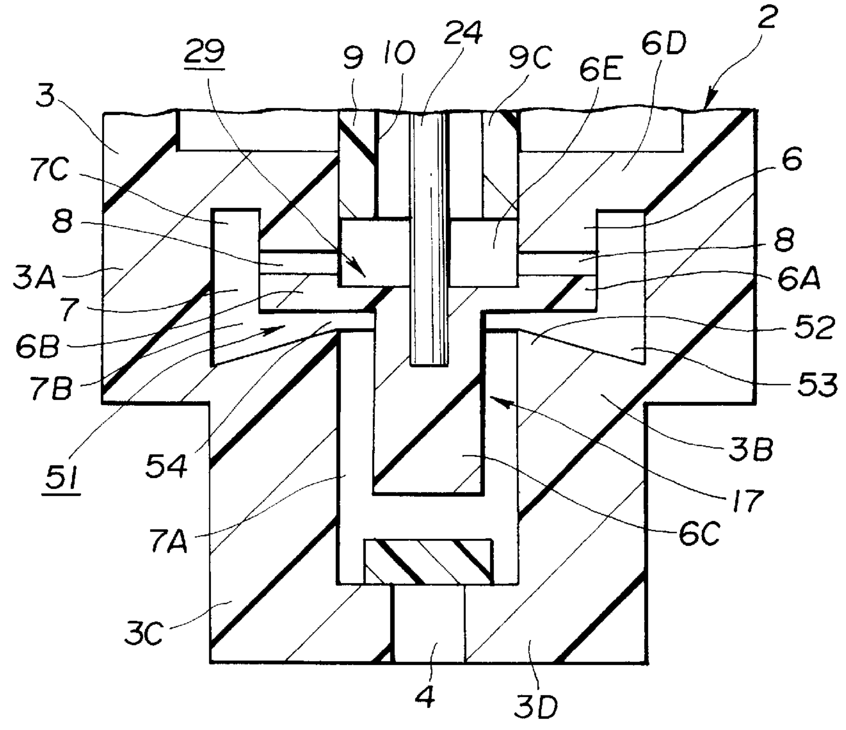
FIG. 7 is a cross sectional view of an essential part of the medicator in a first modification of the first embodiment.

FIG. 7 shows a first modification of the medicator in the first embodiment.

As shown in FIG. 7, the reverse flow drug collecting portion 51 may include a tapered projected wall portion 52 disposed in the radially extended passage 7B and projected progressively in the upward direction toward the inner peripheral side of the radially extended passage 7B, a tapered drug collecting space 53 formed on the tapered projected wall portion 52, and the throttling passage 54 formed between the tapered projected wall portion 52 and the bottom portion 3B of the outer envelope portion 3.

Figure 8:
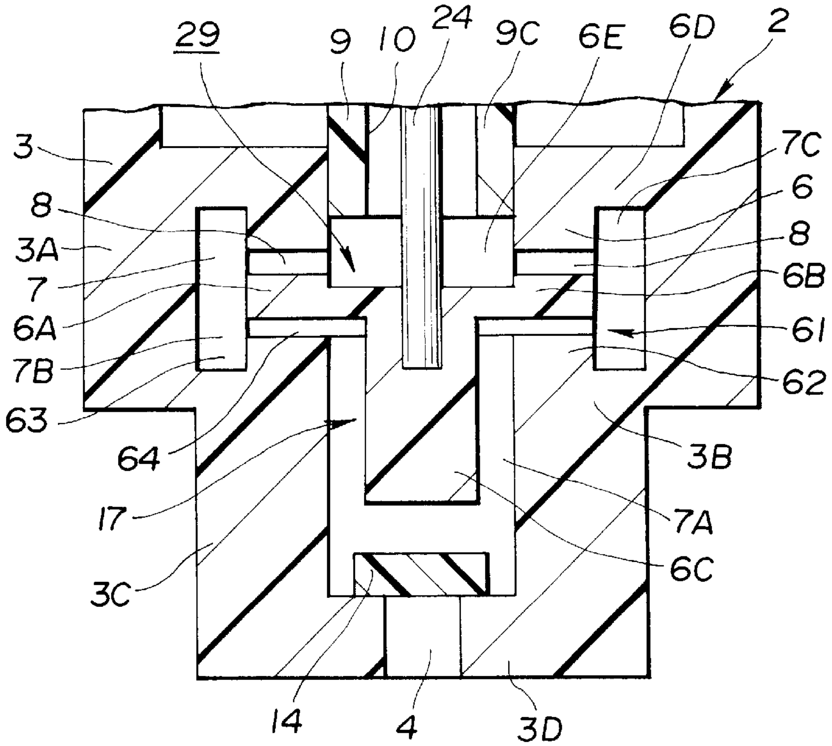
FIG. 8 is a cross sectional view of an essential part of the medicator in a second modification of the first embodiment.

FIG. 8 shows a second modification of the medicator in the first embodiment.

As shown in FIG. 8, the reverse streamed drug collecting portion 61 may include a projected wall portion 62 having a thickness in the radial direction thereof, a convex annular drug collecting space 63 defined by the projected wall portion 62 so as to be continued toward the downward side of the large-diameter axial direction passage 7C of the bend passage 7B, and a throttling passage 64 formed between the projected wall portion 62 and the bottom portion 3B of the outer envelope portion 3.

Figure 9:
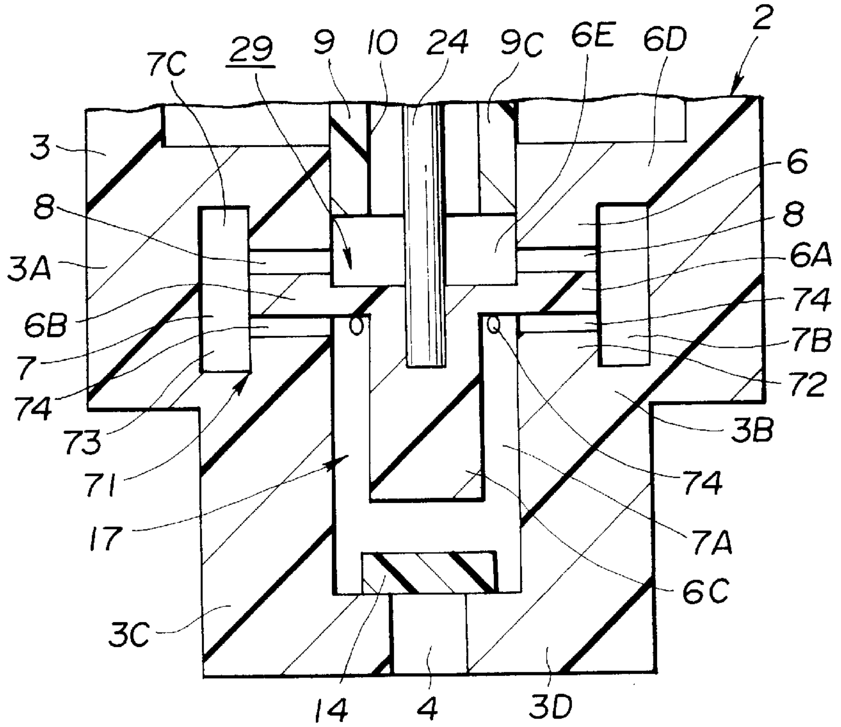
FIG. 9 is a cross sectional view of an essential part of the medicator in a third modification of the first embodiment.

FIG. 9 shows a third modification of the medicator in the first preferred embodiment.

As shown in FIG. 9, the reverse streamed drug collecting portion 71 may include a projected wall portion 72 formed from the bottom portion 3B of the outer envelope portion 3 up to the bottom portion 6B of the inner envelope portion 6, a drug collecting space 73 defined by the projected wall portion 72, and a plurality of throttling passages 74, 74,— formed in the radial direction of the projected wall portion 72.

In the respective embodiments of the medicator, the pair of left and right drug passages 22 and 22 are branched within the spray formed passage member 18 and the pair of the left and right nozzle outlets 23 and 23 are directed into the left and right nostrils of the patient so as to simultaneously dose the powdered drug into the nostrils. However, the drug passage may be single so that the dosing of the powdered drug into the nostrils can be carried out alternatingly through the single nozzle outlet.

Although, in the first and second embodiments, the medicator for the capsule in which the powdered drug is filled is applicable to the nostrils of the patient, the present invention is applicable to the medicator used for dosing the powdered drug into an oral cavity of the patient.

What is claimed is:

1. A medicator for a capsule filled with a powdered drug, comprising:

a first member adapted to receive a capsule therein;

a second member, having an air supply valve structure, arranged to communicate with the first member and arranged to operatively discharge air sucked from outside the medicator towards the first member in which a capsule is received;

an air stream passage formed within the first member and the second member to direct air discharged from the air supply valve structure in a direction towards a capsule received by the first member;

a third member removably attached to the first member to spray powdered drug in a capsule out of the medicator with air discharged from the air supply valve structure via the air stream passage;

a drug trapping structure formed in the air stream passage to trap part of powdered drug contained in a capsule which falls down into the drug trapping structure; and a drug collecting structure formed in the air stream passage between the drug trapping structure and the air supply valve structure to collectively dam powdered drug from a capsule which falls in a direction opposite to the first member together with air when the air supply valve structure is in an intermediate state between a fully open state and a fully closed state, thereby preventing powdered drug from entering the air supply valve structure.

2. A medicator as claimed in claim 1, wherein the drug collecting structure comprises a drug collecting space provided in the air stream passage between the drug collecting structure and the air supply valve structure and which forms a bend passage that extends radially from the drug trapping structure, bends towards an axial direction of the second member, and extends radially up to the air supply valve structure.

3. A medicator as claimed in claim 2, wherein a projected wall portion extends from the second member to narrow the drug collecting space at an end of the bend passage toward the air supply valve structure.

4. A medicator as claimed in claim 3, wherein the second member includes a first needle having a tip extended through the drug trapping structure so as to break a bottom end of a capsule received by the first member to allow powdered drug in the capsule to fall into the drug trapping structure, and wherein the air supply valve structure has a projection portion extending in the axial direction of the second member, the projection portion serving as a valve seat of the air supply valve structure, and a valve body movable between a first hole, defining the fully closed state, and the valve seat, defining the fully opened state.

5. A medicator as claimed in claim 4, wherein the second member comprises a pump chamber defined by a flexible member that is bendable under pressure towards an inner space of the pump chamber so that air in the pump chamber is supplied to the air stream passage through the air supply valve structure, the bend passage, and the drug trapping structure.

6. A medicator as claimed in claim 5, wherein the pump chamber includes an air suction valve structure that opens to suck external air from the medicator into the pump chamber when a pressure force, which presses the flexible member towards the inner space of the pump chamber, is released, returning the flexible member to its original shape, and that closes when the pressure force is applied to the flexible member.

7. A medicator as claimed in claim 6, wherein the third member includes at least one drug spraying passage formed from an inlet that communicates a top end of a capsule received by the first member to a nozzle outlet, and a second needle having a tip extending into the third member to break the top end of a capsule.

8. A medicator as claimed in claim 6, wherein the third member includes a pair of left and right spraying passages formed from an inlet that communicates a top end of a capsule received by the first member to a pair of left and right nozzle outlets, and a second needle having a tip extending into the third member to break the top end of a capsule.

9. A medicator as claimed in claim 2, wherein large-diameter and small-diameter projected wall portions extend from the second member to form the drug collecting space in an approximately crank shape in cross section at an end of the bend passage toward the air supply valve structure.

10. A medicator as claimed in claim 2, wherein a tapered projected wall portion extends from the second member to progressively narrow the drug collecting space at an end of the bend passage toward the air supply valve structure.

11. A medicator as claimed in claim 2, wherein a large-diameter projected wall portion extends from the second member to form a throttling passage at an end of the bend passage toward the air supply valve structure.

12. A medicator as claimed in claim 11, wherein a plurality of throttling passages are formed between the bend passage and the air supply valve structure.

* * * * *